United States Patent
Chen (10) Patent No.: US 7,502,692 B2
(45) Date of Patent: Mar. 10, 2009

(54) METHOD AND COMPUTER PROGRAM PRODUCT FOR ESTIMATING TRUE INTRINSIC RELAXATION TIME AND INTERNAL GRADIENT FROM MULTIGRADIENT NMR LOGGING

(75) Inventor: Songhua Chen, Katy, TX (US)

(73) Assignee: Baker Hughes Incorporated, Houston, TX (US)

( * ) Notice: Subject to any disclaimer, the term of this patent is extended or adjusted under 35 U.S.C. 154(b) by 26 days.

(21) Appl. No.: 11/567,828

(22) Filed: Dec. 7, 2006

(65) Prior Publication Data
US 2007/0244648 A1   Oct. 18, 2007

Related U.S. Application Data

(63) Continuation-in-part of application No. 11/403,255, filed on Apr. 13, 2006, now abandoned.

(51) Int. Cl.
*G01V 3/18* (2006.01)
(52) U.S. Cl. .......................................... 702/8
(58) Field of Classification Search ............. 702/8; 324/332–333
See application file for complete search history.

(56) References Cited

U.S. PATENT DOCUMENTS

| | | | |
|---|---|---|---|
| 4,710,713 A | 12/1987 | Strikman | |
| 5,498,960 A | 3/1996 | Vinegar et al. | |
| 5,698,979 A | 12/1997 | Taicher et al. | |
| 5,712,566 A | 1/1998 | Taicher et al. | |
| 6,069,477 A | 5/2000 | Chen et al. | |
| 6,084,408 A | 7/2000 | Chen et al. | |
| 6,215,304 B1 | 4/2001 | Slade | |
| 6,225,803 B1 | 5/2001 | Chen | |
| 6,331,775 B1 | 12/2001 | Thern et al. | |
| 6,388,441 B1 | 5/2002 | Chen | |
| 6,392,409 B1 | 5/2002 | Chen | |
| 6,400,148 B1 | 6/2002 | Meyer et al. | |
| 6,597,170 B1 | 7/2003 | Beard et al. | |
| 6,600,316 B2 | 7/2003 | Chen et al. | |
| 6,603,310 B2 | 8/2003 | Georgi et al. | |
| 6,755,246 B2 | 6/2004 | Chen et al. | |
| 2005/0162162 A1* | 7/2005 | Itskovich et al. | 324/303 |
| 2006/0055043 A1 | 3/2006 | Liaw et al. | |

OTHER PUBLICATIONS

S. Meiboom, et al. "Modified Spin-Echo Method for Measuring Nuclear Relaxation Times" The Review of Scientific Instruments. Phys. Rev. 94, 630 (1954). pp. 688-691.
U.S. Appl. No. 11/403,225, "Method and Computer Program Product for Estimating True Intrinsic Relaxation Time and Internal Gradient From Multigradient NMR Logging". filed Apr. 13, 2006. 26 pages.
Chen, et al. "MR Explorer Log Acquisition Methods: Petrophysical-Objective-Oriented Approaches". SPWLA 44th Annual Logging Symposium, Jun. 22-25, 2003. pp. 1-13.

* cited by examiner

*Primary Examiner*—Bryan Bui
*Assistant Examiner*—Jonathan Teixeira Moffat
(74) *Attorney, Agent, or Firm*—Cantor Colburn LLP (57) ABSTRACT

A method and a computer program product for estimating the true intrinsic relaxation time $T_2$ and the internal gradient $G_{int}$ for a multi-frequency nuclear magnetic resonance imaging tool for well logging includes providing at least two frequencies in a plurality of echo trains, evaluating the signal decay in each echo train, quantifying the signal decay and correlating the signal decay to the internal gradient.

23 Claims, 2 Drawing Sheets

METHOD AND COMPUTER PROGRAM PRODUCT FOR ESTIMATING TRUE INTRINSIC RELAXATION TIME AND INTERNAL GRADIENT FROM MULTIGRADIENT NMR LOGGING

CROSS REFERENCE TO RELATED APPLICATION

This application is filed under 35 U.S.C. 120 and 37 CFR §1.53(b) as a Continuation-In-Part of copending U.S. patent application Ser. No. 11/403,255, filed Apr. 13, 2006 and claims priority thereto. The disclosure of U.S. patent application Ser. No. 11/403,255 is incorporated by reference herein in its entirety.

BACKGROUND OF THE INVENTION

1. Field of the Invention

The invention relates to geological exploration techniques and more specifically to estimation of geologic properties from well logging data.

2. Description of the Related Art

Various instruments applying Nuclear Magnetic Resonance (NMR) imaging technology are useful for measuring certain petrophysical properties of earth formations. NMR well logging instruments typically include a magnet for polarizing nuclei in the earth formations surrounding a wellbore. The polarizing typically occurs along a static magnetic field through use of at least one antenna for transmitting radio frequency ("RF") energy pulses into the formations. The RF pulses reorient the spin axes of certain nuclei in the earth formations in a predetermined direction. As the spin axes precess and reorient themselves into alignment with the static magnetic field, RF energy is emitted and can be detected by the antenna. The magnitude of the RF energy emitted by the precessing nuclei and the rate at which the magnitude changes are related to certain petrophysical properties of interest in the earth formations.

A typical embodiment of an NMR logging tool for characterization of geologic deposits includes a side-looking or centralized NMR logging tool. Typically, the tool operates using a gradient magnetic field and multiple frequencies. One example of such a tool is the MX Explorer$^{SM}$ provided by Baker Hughes, Inc. of Houston Tex. (referred to as the "MREX tool," the "logging tool" or simply as the "tool" herein).

There are several principal operating parameters in NMR well logging which should be optimized for efficient operation of an NMR well logging instrument. These parameters include the logging speed (speed of motion of the instrument along the wellbore), the average and the peak power supplied to the instrument and transmitted as RF pulses, and the signal-to-noise ratio ("SNR"). Other parameters of interest include the vertical resolution of the instrument and the radial depth of investigation of the measurements made by the instrument within the formations surrounding the wellbore.

Physical parameters of particular interest to wellbore operators are the fractional volume of pore spaces in the earth formations ("porosity"), the texture of the rock and connectivity of the pore spaces, and the nature of the fluids contained in the pore spaces. In petroleum bearing earth formations, the pore spaces will typically contain some fractional volume of water and some fractional volume of hydrocarbons. Since hydrocarbons generally have different NMR relaxation properties than water, various NMR relaxometry techniques have been developed to qualitatively determine the nature of the fluids present in certain earth formations.

One method, for example, enables discriminating between gas and oil, and light oil and water. This method includes performing NMR spin-echo experiments using two different "wait times", $T_w$. The wait time $T_w$ is the delay between individual Carr-Purcell-Meiboom-Gill ("CPMG") spin echo measurement sequences. See S. Meiboom et al, Rev. of Sci. Instr. v. 29, p. 6881 (1958). Another technique, described in U.S. Pat. No. 5,498,960 issued to Vinegar et al, uses two different inter-echo spacing times, TE, for CPMG sequences measured in a gradient magnetic field. Typically, the inter-echo spacing is the time between rephasing radio frequency (RF) energy pulses applied to the logging instrument's antenna to "rephase" precessing nuclei which are influenced by the NMR survey. The rephasing RF pulses result in the "spin echoes" whose amplitude is measured. Gas, oil and water generally have different self-diffusivities, and these differences will be reflected in differences in the apparent transverse relaxation time $T_2$ calculated for an earth formation between CPMG sequences measured using different values of TE. The technique described in the Vinegar et al '960 patent for discriminating types of fluids in pore spaces of earth formations typically uses two values of TE.

Another physical property of particular interest is the viscosity of any oil which may be present in the pore spaces of the earth formation. A relationship between an intrinsic transverse relaxation time, $T_{2int}$, for oil with respect to its viscosity, $\eta$ is provided:

$$T_{2int} = \frac{1.2 T_K}{298 \eta^x}; \qquad (1)$$

where $T_K$ represents the absolute temperature (in ° K) of the oil and x represents an empirical fit factor, typically about equal to unity. A difficulty in determining oil viscosity $\eta$ using this relationship is that it requires determining the intrinsic transverse relaxation time $T_{2int}$. For NMR logging instruments that use a gradient static magnetic field, the transverse relaxation time $T_2$ calculated from spin-echo amplitude measurements is affected by a self-diffusion effect $T_{2D}$. An apparent transverse relaxation time $T_2$ calculated from the spin echo amplitudes is related to the intrinsic transverse relaxation time $T_{2int}$ in the following manner:

$$\frac{1}{T_2} = \frac{1}{T_{2int}} + \frac{1}{T_{2D}}; \qquad (2)$$

where the self-diffusion effect $T_{2D}$ can be determined by the expression:

$$\frac{1}{T_{2D}} = \frac{D(\gamma * TE * G_Z)^2}{12}; \qquad (3)$$

where an inter-echo time TE is generally selected by the system operator and has a known value; D represents a diffusivity of the media; the gyromagnetic ratio $\gamma$ is unique for each nuclear isotope; and the magnetic field gradient $G_Z$, is dependent upon a frequency (f) and includes an internal gradient component $G_{int}$ and an external gradient component $G_{MREX}$. The magnitude of the static magnetic field, $B_0$, in which the CPMG sequences are actually measured, is therefore controlled by selection of a frequency for the RF pulses. Since the spatial distribution of the static magnetic field amplitude and gradient magnitude are known, the gradient of the static magnetic field in the NMR excitation volume will also be known for any selected RF excitation frequency. The actual magnetic field gradient within the pore spaces of the earth formation may not be known, however, since the field gradients internal to the pore spaces depend on differences in magnetic susceptibility between the formation solids ("matrix") and the fluid in the pore spaces, as well as the amplitude of the static magnetic field. See for example, U.S. Pat. No. 5,698,979 issued to Taicher et al.

Determination of the internal gradient $G_{int}(f)$ of the static magnetic field $B_0$ is essential for accurate material typing using diffusion-based NMR techniques. Since the internal gradient $G_{int}(f)$ is related to the pore mineralogy and pore geometry, the internal gradient $G_{int}(f)$ may also be used to obtain additional information about properties of the porous rock.

The internal gradient $G_{int}(f)$ in porous media arises from differences in the magnetic properties between minerals in the formation matrix and material (e.g., fluid) in pore spaces of the formation. Mathematically, the internal gradient $G_{int}(f)$ is described as:

$$G_{int} \propto \frac{\Delta\chi \cdot B_0}{r}; \qquad (4)$$

where $1/r$ represents the curvature of a pore within the formation, where $\Delta_\chi$ represents magnetic properties in the formation (also referred to as a "susceptibility difference" between the matrix and the fluid) and $B_0$ represents an applied static magnetic field. Although $\Delta_\chi$ is theoretically a dispersive quantity, for the low-frequency range of NMR logging interest, it can be regarded as typically being frequency independent. The internal gradient $G_{int}$ is therefore dependent upon the static-field $B_0$. Consequently, for a logging tool that makes use of multiple frequencies to generate a gradient magnetic field, the internal gradient $G_{int}$ is also frequency dependent.

The effective gradient along the field direction $G_{int}(f)$ may therefore be described as:

$$G(f) = G_{z,int}(f) + G_{MREX}(f) = a \cdot \frac{2\pi f \cdot \Delta\chi}{\gamma \cdot r} + b \cdot f^c; \qquad (5)$$

Where G represents a radiofrequency (RF) field gradient strength; a is substantially equal to unity, while b and c are two coefficients dependent on aspects of the NMR logging instrument. For an MREX logging tool, b is approximately 40 and c is approximately 1.5. This function includes two operands, where the first operand $G_{z,int}(f)$ represents the internal magnetic field gradient and $G_{MREX}(f)$ represents the logging tool magnetic field gradient (also referred to as an "external magnetic field gradient").

Eq. (5) shows that both the internal gradient $G_{int}(f)$ and the tool gradient $G_{MREX}(f)$ are frequency dependent. However, these dependencies are different. The internal gradient $G_{z,int}(f)$ is linearly proportional to f, but the tool gradient $G_{MREX}(f)$ generally depends upon frequency more than linearity. In the prior art, typical diffusion based NMR fluid typing techniques acquire multiple G(f)*TE echo trains for hydrocarbon typing where G(f) has always been simplified to the tool gradient $G_{MREX}(f)$ and a contribution by the internal gradient $G_{int}(f)$ has been discounted. Inherently, this assumption causes inaccuracies in results.

What is needed is a technique for accurately determining the internal magnetic field gradient $G_{z,int}(f)$ of the earth formation for a given NMR well logging tool and operating frequency, which will in turn provide for accurate typing of materials (fluids as well as minerals) of formations using diffusion based NMR techniques.

BRIEF SUMMARY OF THE INVENTION

Disclosed is a method for estimating an internal gradient of an earth formation in response to a magnetic field, that includes: applying the magnetic field to the earth formation; directing pulsed RF energy for a first frequency to the earth formation and acquiring a first signal and directing pulsed RF energy to the earth formation for a second frequency and acquiring a second signal; determining a first signal decay corresponding to the first signal and a second signal decay corresponding to the second signal; and using the first signal decay and the second signal decay to estimate the internal gradient.

Also disclosed is a computer program product for estimating an internal gradient of an earth formation in response to a magnetic field, that includes instructions for: applying the magnetic field to the earth formation; directing pulsed RF energy for a first frequency to the earth formation and acquiring a first signal and directing pulsed RF energy to the earth formation for a second frequency and acquiring a second signal; determining a first signal decay corresponding to the first signal and a second signal decay corresponding to the second signal; using the first signal decay and the second signal decay to estimate the internal gradient; and providing the estimation as an output.

In addition, a method for typing a material using diffusion based nuclear magnetic resonance (NMR) techniques, is disclosed and includes: determining an internal gradient of a magnetic field; and estimating a material type for the material based on the internal gradient.

Other systems, methods, and/or computer program products according to embodiments will be or become apparent to one with skill in the art upon review of the following drawings and detailed description. It is intended that all such additional systems, methods, and/or computer program products be included within this description, be within the scope of the present invention, and be protected by the accompanying claims.

BRIEF DESCRIPTION OF THE DRAWINGS

For detailed understanding of the present invention, references should be made to the following Detailed Description of the Invention, taken in conjunction with the accompanying drawings, in which like elements have been given like numerals, wherein.

The detailed description explains the preferred embodiments of the invention, together with advantages and features, by way of example with reference to the drawings.

DETAILED DESCRIPTION OF THE INVENTION

Figure 1:
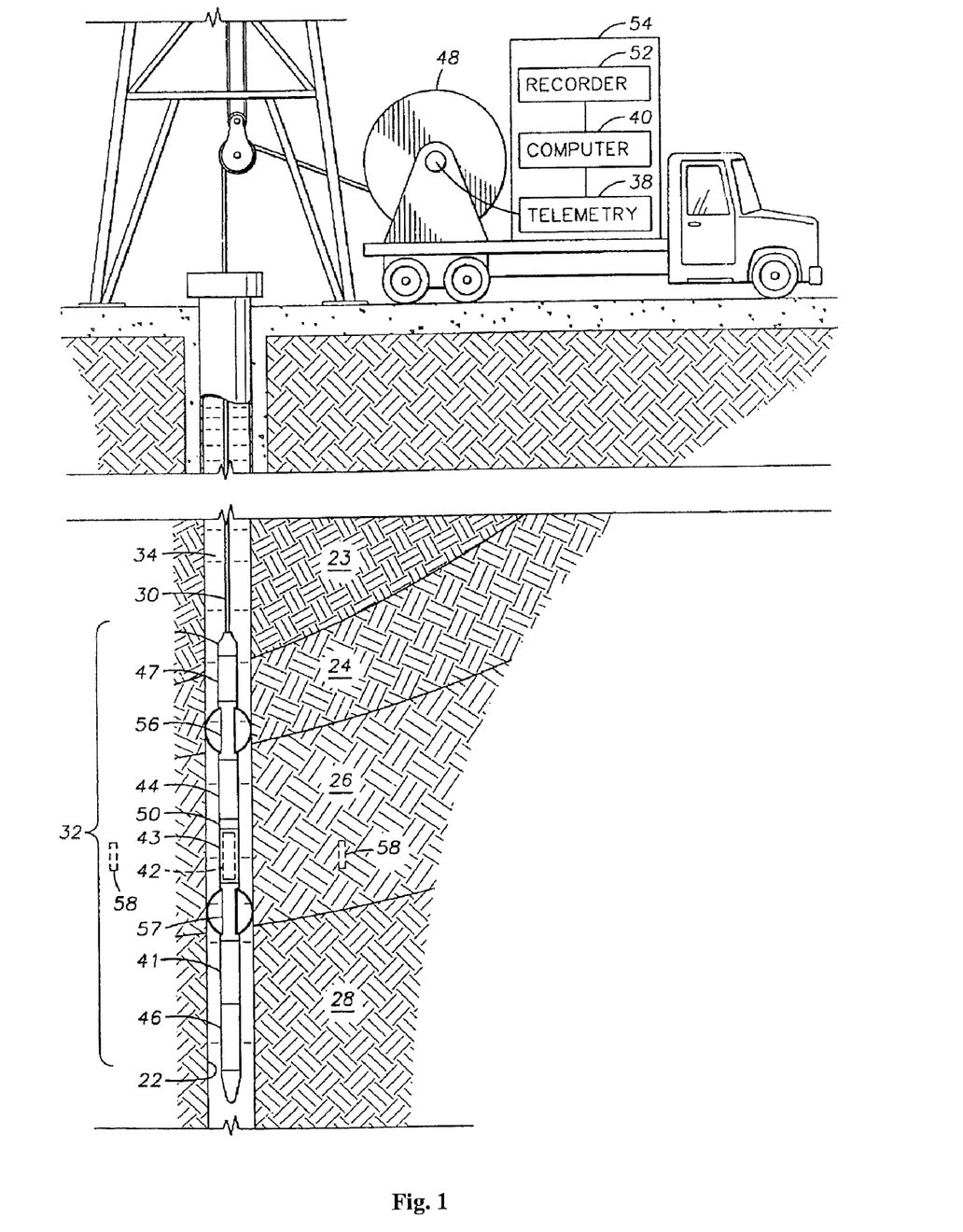
FIG. 1 depicts aspects of an NMR logging tool in a wellbore.

FIG. 1 shows a well logging apparatus disposed in a wellbore 22 penetrating earth formations 23, 24, 26, 28 for making measurements of properties of the earth formations 23, 24, 26, 28. The wellbore 22 in FIG. 1 is typically filled with a fluid 34 known in the art as "drilling mud." A "sensitive volume," shown generally at 58 and having a generally cylindrical shape, is disposed in one of the earth formations, shown at 26. The sensitive volume 58 is a predetermined portion of the earth formations 26 in which nuclear magnetic resonance (NMR) measurements are made, as will be further explained.

In typical embodiments, the sensitive volume 58 includes materials such as would be found within a wellbore 22 including a mixture of liquids including water, (including fresh water and salt water), drilling fluid, minerals, clay, mud, oil and formation fluids that are indigenous to the formations 23, 24, 26, 28, or introduced therein. NMR measurements may be used to determine a variety of formation properties and other aspects of interest. For example, aspects of mineralogy may be determined or surmised. Consider the following.

An internal magnetic field gradient in a rock formation arises from differing properties of the minerals that form the rock matrix and the fluids that fill pore spaces. The magnetic susceptibility $\chi$ of water ($H_2O$) is very small, and has been reported to be about $-12.97E-06$ cgs at room temperature. The basic minerals forming sandstones and carbonate rocks also have small magnetic susceptibilities. For example, silicon dioxide ($SiO_2$) has a magnetic susceptibility $\chi$ value of about $-19.6E-06$ cgs and calcium carbonate ($CaCO_3$) has a magnetic susceptibility $\chi$ value of about $-38.2E-06$ cgs. Both minerals have magnetic susceptibility $\chi$ close to that of water. On the other hand, manganese compounds, such as $Mn_2O_3$, have a magnetic susceptibility $\chi$ value of thousand times higher than that of water or quartz. Thus, the presence of manganese compounds can strongly affect internal gradients measured in the rock formation. Further, a spike in internal gradient values for a zone in the formation may indicate some mineralogy variation within the formation zone. Note that the magnetic susceptibility $\chi$ values were cited from the "CRC Handbook of Chemistry and Physics," $63^{rd}$ edition, CRC Press, 1982.

Exemplary minerals for typing include at least one of detrital minerals comprising $SiO_2$, $Ca_2CO_3$, $Mn_2O_3$ and secondary minerals comprising at least one of a type of clay mineral and a type of evaporate mineral.

The magnitude of the measured internal gradient is dependent on other factors as well. For example, the internal gradient is effected by the curvature of the interface between pore fluid and the rock matrix surface. Thus, the internal gradient is also related to pore geometry. More specifically, for identical minerals, the smaller the pores, the larger the internal gradient. This may provide for certain determinations. For example, for carbonate rocks, the internal gradient may only be significant in the intragranualar pores, and thus may be helpful for surveys of the intragraualar pores.

Many sandstone formation rocks contain certain amount of clay minerals. The distribution of clay minerals may affect the pore geometry significantly. Therefore, the internal gradient is significantly larger for dispersed clay minerals than for structural clay distributions. This is because the former introduces a great amount of surface area interfacing with pore fluid and increases curvature on the interfaces. Thus, if the amount of clay is determined by NMR clay-volumetric measurements or other mineral-sensitive measurements, one will be able to use the internal gradient estimates to predict the clay distributions.

NMR relaxation time distribution is often known to be associated with the pore size distribution in rocks. This association is valid if the surface relaxivity is relatively uniform over different pore sizes. If different sized-pores are confined by different minerals that have a different magnetic susceptibility $\chi$, one needs first to correct the internal gradient effect before the pore size distribution can be derived from NMR relaxation time. Therefore, determination of the internal gradient is essential for accurate determination of pore size distributions.

Turning again to FIG. 1, a string of logging tools 32, which can include an NMR apparatus according to the present invention, is typically lowered into the wellbore 22 by a means of an armored electrical cable 30. The cable 30 can be spooled and unspooled from a winch or drum 48. The tool string 32 can be electrically connected to surface equipment 54 by an insulated electrical conductor (not shown separately in FIG. 1) forming part of the cable 30. The surface equipment 54 can include one part of a telemetry system 38 for communicating control signals and data to the tool string 32 and computer 40. The computer may also include a data recorder 52 for recording measurements made by the apparatus and transmitted to the surface equipment 54. Typically, the computer includes a variety of input/output devices and other supporting devices to enhance the operation of the apparatus and estimations performed by use thereof.

An NMR probe 42 can be included in the tool string 32. The tool string 32 is typically centered within the wellbore 22 by means of a top centralizer 56 and a bottom centralizer 57 attached to the tool string 32 at axially spaced apart locations. The centralizers 56, 57 can be of types known in the art such as bowsprings.

Circuitry for operating the NMR probe 42 can be located within an NMR electronics cartridge 44. The circuitry can be connected to the NMR probe 42 through a connector 50. The NMR probe 42 is typically located within a protective housing 43 which is designed to exclude the drilling mud 34 from the interior of the probe 42. The function of the probe 42 will be further explained.

Other well logging sensors (not shown separately for clarity of the illustration in FIG. 1) may form part of the tool string 32. As shown in FIG. 1, one additional logging sensor 47 may be located above the NMR electronics cartridge 44. Other logging sensors, such as shown at 41 and 46 may be located within or below the bottom centralizer 57. The other sensors 41, 46, 47 can be of types familiar to those skilled in the art and can include, but are not limited to, gamma ray detectors, formation bulk density sensors or neutron porosity detectors. Alternatively, parts of the NMR electronics may be located within electronic cartridges which form part of other logging sensors. The locations of the other sensors 41, 46, 47 shown in FIG. 1 are a matter of convenience for the system designer and are merely exemplary.

Other aspects of the exemplary embodiment of the NMR probe 42 are provided in U.S. Pat. No. 5,712,566, entitled "Nuclear Magnetic Resonance Apparatus and Method," issued Jan. 27, 1998 to Taicher et al., and incorporated herein by reference in it's entirety. Another non-limiting example is disclosed in U.S. Pat. No. 4,710,713, also issued to Taicher et al, and incorporated by reference herein in it's entirety. It should be recognized that these embodiments of NMR tools are exemplary only, and not limiting of the teachings herein.

The techniques disclosed herein provide for improved estimations where the formations 23, 24, 26, 28 are macroscopically uniform within a depth of interest within sensitive volume 58 the NMR logging tool. That is, pore geometry and mineralogy may vary microscopically, but on average, each depth of interest within the sensitive volume 58 has considerably similar mineralogy and pore geometry effect, or can be represented with an effective pore geometry and mineralogy for a given depth in the wellbore 22.

Figure 2:
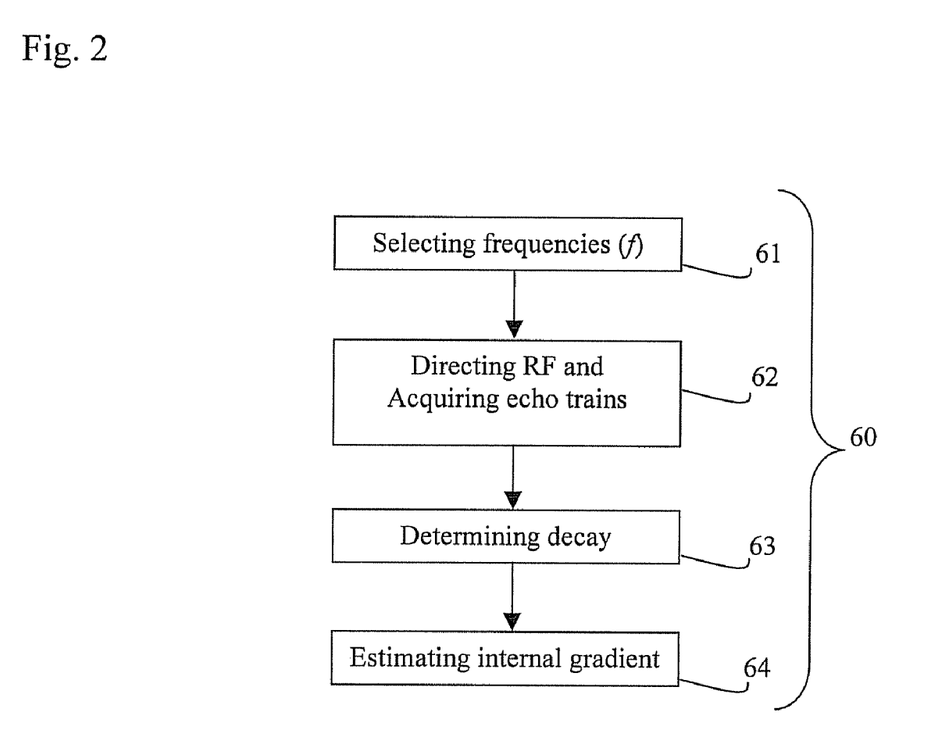
FIG. 2 depicts aspects of a method for estimating the internal gradient $G_{z,int}$ of a magnetic field $B_0$.

FIG. 2 provides a summary of aspects of an exemplary embodiment of a method for determining the internal gradient $G_{int}$. Internal gradient $G_{int}$ estimation 60 first calls for selecting frequencies 61. Using the selected frequencies ($f_1$, $f_2$, . . . ), directing RF energy and acquiring echo trains 62 is performed. Directing RF energy and acquiring echo trains 62 involves, among other things, generating and directing pulses of radiofrequency (RF) energy into the earth formations 23, 24, 26, 28 and then acquiring and resolving the pulsed RF energy as the echo trains.

It should be recognized that use of an "echo train" is merely illustrative. That is, it should be recognized that a portion of an echo train may be used in support of the teachings herein. Accordingly, while use of the first echo train and the second echo train may be typically called for, in some embodiments, only the portion is used. Therefore, acquiring an echo train 62 should be construed to mean acquiring any signal or portion of a signal (corresponding to the directing of the RF energy) that provides for determining decay 63.

When the signals from the echo trains are detected, the signals are evaluated and determining decay 63 for the signals is completed. By using the determination information, estimating internal gradient 64 is completed. As selecting frequencies 61 as well as directing RF energy and acquiring an echo train 62 are generally understood by users of multi-frequency NMR probes 42, further discussion is not warranted. However, steps to determining decay 63 and estimating internal gradient 64 are described in greater detail below.

As a matter of convention, one should note that the variables used herein are not redefined, and appear throughout the disclosure. Accordingly, previously defined variables are generally not reintroduced. For convenience of referencing, the following representations are some of the definitions applied herein: $B_0$ represents static field strength; $B_1$ represents RF field strength; D represents diffusivity; e,E represents echo amplitude with and without noise included; f represents frequency; G represents RF field gradient strength; L represents echo length ($N_E \cdot T_E$); M represents echo magnetization amplitude; $N_E$ represents a number of echoes in an echo train; $S_E$ represents a sum of echoes; $T_1$ represents a longitudinal relaxation time; $T_2$ represents a transverse relaxation time; $T_{2B}$ represents a bulk fluid transverse relaxation time; $T_{2cutoff}$ represents a dividing time; $T_{2diff}$ represents an extra decay time factor due to diffusion; $T_{2int}$ represents an intrinsic relaxation time; $T_{2surf}$ represents a surface relaxation time; $T_E$ represents an interecho time; $T_W$ represents a wait time; and $t_k$ represents the time at the formation of the $k^{th}$ echo.

First, a derivation of the internal field gradient $G_{z,int}(f)$ is provided. Using the above relationship of Eq. (5), the internal gradient $G_{z,int}(f)$ and the tool gradient $G_{MREX}(f)$ are squared to obtain:

$$G^2(f) = (G_{int} + G_{MREX})^2 = G_{int}^2 + G_{MREX}^2 + 2\vec{G}_{int} \cdot \vec{G}_{MREX} \quad (6);$$

and, on the average, the cross term ($2G_{int} \cdot G_{MREX}$) cancels out to account for random orientation. Thus:

$$\overline{G}^2(f) \approx G_{int}^2 + G_{MREX}^2 \quad (7).$$

Plugging Eq. (7) into Eq. (3), one obtains:

$$\frac{1}{T_{2D}} = \frac{D(\gamma \cdot G_{int} \cdot TE)^2}{12} + \frac{D(\gamma \cdot G_{MREX} \cdot TE)^2}{12}. \quad (8)$$

One skilled in the art will recognize that multiple measurements of inter-echo times TE do not provide for determination of the internal gradient $G_{z,int}(f)$ and the tool gradient $G_{MREX}(f)$ directly. Accordingly, Eq. (2) is rewritten using Eq. (8) as:

$$T_2^{-1} = T_{2,int}^{-1} + \frac{D(\gamma \cdot G_{int} \cdot TE)^2}{12} + \frac{D(\gamma \cdot G_{MREX} \cdot TE)^2}{12} \quad (9)$$
$$= \left[ T_{2,int}^{-1} + \frac{D(\gamma \cdot G_{MREX} \cdot TE)^2}{12} \right] + \frac{D(\gamma \cdot G_{int} \cdot TE)^2}{12}.$$

The method as disclosed herein includes at least two measurements completed by selecting at least two frequencies f and two different inter-echo times TE. In these measurements, the product of tool gradient $G_{MREX}$ and the inter-echo time TE is held constant. This relationship is expressed as:

$$G_{MREX}(f_1) \cdot TE_1 = G_{MREX}(f_2) \cdot TE_2 \quad (10).$$

If it is assumed that:

$$G_{MREX}(f_1) = 2G_{MREX}(f_2) \quad (11); \text{ and}$$

$$TE_1 = 0.5 TE_2 \quad (12),$$

then, according to Eq. (5), $$\frac{f_1}{f_2} = 2^{1/c}; \quad (13)$$

where, for the MREX tool having a value for c that is approximately 1.5, the frequency ratio ($f_1/f_2$) is approximately 1.59. A corresponding change in the internal gradient $G_{int}$ (for the two frequencies) may be described as:

$$G_{int,1} = (f_1/f_2) \cdot G_{int,2} = 1.59 \cdot G_{int,2} \quad (14); \text{ and,}$$

$$(G_{int,1} \cdot TE)_1/(G_{int,2} \cdot TE_2) \approx 0.795 \quad (15).$$

If the internal gradient $G_{int}$ effect is much smaller than the external (tool) gradient $G_{MREX}$, then both echo trains (one for each of the selected frequencies $f_1$, $f_2$) should produce nearly identical results. On the other hand, if the internal gradient $G_{int}$ dominates, the echo train with $G_{int,2} \cdot TE_2$ decays faster than the echo train with $G_{int,2} \cdot TE_2$. For each echo train, echo decay $E_k$ may be described as:

$$E_k = M_0 \cdot \exp\left(-\frac{t_k}{T_2}\right) \quad (16)$$
$$= M_0 \cdot \exp\left(-\left(\frac{1}{T_{2int}} + \frac{D(\gamma \cdot G_{MREX} \cdot TE)^2}{12}\right) t_k\right) \cdot$$
$$\exp\left(-\frac{D(\gamma \cdot G_{int} \cdot TE)^2 t_k}{12}\right);$$

and can be quantified and related to the value for the internal gradient $G_{int}$. That is, in Eq. (16), only the exponential factor $$\exp\left(-\frac{D(\gamma \cdot G_{int} \cdot TE)^2 t_k}{12}\right)$$

is different for the measurements taken at $f_1$, $f_2$. Note that in Eq. (16) $M_0$ represents an initial echo magnetization amplitude and $t_k$ represents time at the formation of the $k^{th}$ echo.

Consequently, the internal gradient $G_{int}$ is quantified by a difference in the decay rate. For instance, a ratio of the echo decay $E_{k,1}$ and echo decay $E_{k,2}$ measurements is described as:

$$\frac{E_{k,1}}{E_{k,2}} = \exp\left(-\frac{D(\gamma \cdot G_{int,1} \cdot TE_1)^2 t_k}{12}\right) / \exp\left(-\frac{D(\gamma \cdot G_{int,2} \cdot TE_2)^2 t_k}{12}\right)$$
$$= \exp\left(+\frac{\xi \cdot D(\gamma \cdot G_{int,2} \cdot TE_2)^2 t_k}{12}\right). \quad (17)$$

where $\xi$ represents a configuration coefficient that is generally dependent upon the selection of the tool gradient $G_{MREX}$ and the inter-echo time TE. In embodiments where the parameters of Eq. (11) and Eq. (12) are used, the configuration coefficient $\xi$ is 0.368. More specifically, the configuration coefficient $\xi=0.368$ if $G_{MREX}(f_1)=2G_{MREX}(f_2)$ and $TE_1=0.5\ TE_2$.

Accordingly, Eq. (17) provides one exemplary and non-limiting calculation for estimating internal gradient 64. That is, after the computer 40 has completed signal processing and other steps to complete determining decay 63, Eq. (17), as an example, may be used to derive the internal gradient $G_{int}$.

For a given fluid having a diffusion constant D, whose properties are known, the only unknown in Eq. (17) is the internal gradient $G_{int}$. Those skilled in the art will recognize that using a ratio to solve the Eq. (17) is not the only approach. In another approach, Eq. (12) and Eq. (17) can be solved simultaneously to obtain the internal gradient $G_{int}$. Furthermore, a similar approach can be extended to multiple transverse relaxation time $T_2$ components where an inversion technique is applied to obtain the distribution of apparent transverse relaxation time $T_2$ (Eq. (2)) values for the two measurements. As an example, two incremental transverse relaxation time $T_2$ distributions are defined as distribution $P_1(T_{2int},T_{2D}(G_{int,1}))$ and distribution $P_2(T_{2int},T_{2D}(G_{int,2}))$, respectively. Using these distributions, one can compute the log-mean transverse relaxation time $T_{2LM}$ from distribution $P_1$ and distribution $P_2$, and consequently the overall internal gradient $G_{int}$ can be computed from Eq. (2) as:

$$\frac{1}{T_{2LM,1}} - \frac{1}{T_{2LM,2}} = \frac{\xi \cdot D(\gamma \cdot TE_2 \cdot G_{int,2})^2}{12}. \quad (18)$$

If different fluids can be separated from the incremental transverse relaxation time $T_2$ distributions, the log-mean transverse relaxation time $T_2$ can be computed for individual fluids and materials. Consequently, values for the internal gradient $G_{int}$ can then be obtained from Eq. (18).

As discussed herein, an "echo train" refers to the series of echoes corresponding to a selected frequency $f_x$. Manipulation of the inter-echo times TE for each echo train (that is, between at least two selected frequencies $f_1, f_2$), as discussed in the foregoing example, provide for comparison of results and the derivation of the internal field $G_{int}$.

The above approach can be extended to include varying pairs of echo trains having inter-echo times $TE_1$ and $TE_2$. In one embodiment, both inter-echo times $TE_1$ and $TE_2$ are increased proportionally. For example, consider inter-echo times $TE_3=3TE_1$ and $TE_4=3TE_2$, such that Eq. (10) and Eq. (12) remain valid. Because long inter-echo times TE effectively excluded the shortest relaxation components, one will be able to compute the internal gradient $G_{int}$ that corresponds to non-clay bound water components (i.e., the effective internal gradient $G_{int}$ for sands).

In another embodiment, it is assumed that the echo trains from the above embodiments are related as follows: $TE_2=2TE_1$, $TE_3=3TE_1$ and $TE_4=6TE_1$. Note that in this example, the ratios of 1:2, 1:3, and 1:6 used here are arbitrary and other numbers are possible, subject to the operating frequencies for the logging tool.

In this example, the initial echoes from the inter-echo times $TE_1$, $TE_2$, and $TE_3$ are discarded so that all first useful echoes in the data processing starts at inter-echo time $TE_4$. Thus, substantial sensitivity for the same range of components in the transverse relaxation time $T_2$ is realized. Accordingly, this relationship may be expressed as:

$$G_{int,1} \cdot TE_1 : G_{int,2} \cdot TE_2 : G_{int,1} \cdot TE_3 : G_{int,2} \cdot TE_4 = 0.796 : 1 : 2.38 : 3. \quad (19).$$

Another embodiment calls for adjusting estimations of the internal gradient $G_{int}$ without varying the inter-echo time TE. In this embodiment, the only limitation is that the ratio of change in the inter-echo time TE is limited by a useful range of the tool and thus, the external gradient $G_{MREX}$ variation range.

Those familiar with the technology will recognize that varying the combination of the inter-echo times TE and selected frequencies (f) can provide for cross-checking of estimations, improved results, and provide other such advantages.

Effects from the internal gradient $G_{int}$ are typically important when the strength of internal gradient $G_{int}$ is comparable to or larger than the tool gradient $G_{MREX}$. Thus, the technique described is useful for the range of internal gradient $G_{int}$ as encountered in well logging.

The teachings herein provide for separating the internal magnetic field gradient $G_{z,int}(f)$ effects from the external magnetic field gradient $G_{MREX}$ effects using a method that takes advantage of unique aspects of a multi-frequency NMR probe 42. By separately determining the internal gradient $G_{z,int}(f)$ a true intrinsic relaxation time $T_{2,int}$ can be estimated.

The teachings herein provide for, among others, embodiments in the form of computer-implemented processes and apparatuses for practicing those processes. In exemplary embodiments, the invention is embodied in computer program code executed by one or more network elements. Embodiments include computer program code containing instructions embodied in tangible media, such as floppy diskettes, CD-ROMs, hard drives, or any other computer-readable storage medium, wherein, when the computer program code is loaded into and executed by a computer, the computer becomes an apparatus for practicing the invention. Embodiments include computer program code, for example, whether stored in a storage medium, loaded into and/or executed by a computer, or transmitted over some transmission medium, such as over electrical wiring or cabling, through fiber optics, or via electromagnetic radiation, wherein, when the computer program code is loaded into and executed by a computer, the computer becomes an apparatus for practicing the invention.

When implemented on a general-purpose microprocessor, the computer program code segments configure the microprocessor to create specific logic circuits. Output may be directed to a variety of devices as are known in the art, including, as non-limiting examples, at least one of a screen, a printer, a memory, a network, a storage, a wireless link and a direct link.

Further, while the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

What is claimed is:

1. A method for estimating an internal gradient of an earth formation in response to a magnetic field, the method comprising:
    applying the magnetic field to the earth formation;
    directing pulsed RF energy for a first frequency to the earth formation and acquiring a first signal and directing pulsed RF energy to the earth formation for a second frequency and acquiring a second signal;
    determining a first signal decay corresponding to the first signal and a second signal decay corresponding to the second signal; and
using the first signal decay and the second signal decay to estimate the internal gradient, wherein using the determinations comprises solving a relationship for the internal gradient, $G_{int}$, the relationship comprising:

$$\frac{E_{k,1}}{E_{k,2}} = \exp\left(-\frac{D(\gamma \cdot G_{int,1} \cdot TE_1)^2 t_k}{12}\right) \Big/ \exp\left(-\frac{D(\gamma \cdot G_{int,2} \cdot TE_2)^2 t_k}{12}\right);$$

where
$E_{k,1}$ represents the first signal decay;
$E_{k,2}$ represents the second signal decay;
$TE_1$ represents a signal time for the first signal;
$TE_2$ represents a signal time for the second signal;
D represents a diffusion constant;
$\gamma$ represents a gyromagnetic ratio;
$t_k$ represents time at a formation of a $k^{th}$ echo;
$G_{int,1}$ represents the internal gradient for the first frequency; and
$G_{int,2}$ represents the internal gradient for the second frequency.

2. The method as in claim 1, wherein at least one of the first signal and the second signal comprise one of an echo-train and a portion of an echo-train.

3. The method as in claim 1, wherein directing pulsed RF energy for the second frequency comprises directing pulsed RF energy comprising signal times that are proportionally related to signal times of the pulsed RF energy for the first frequency.

4. The method as in claim 3, wherein each of the signal times comprises inter-echo times.

5. The method as in claim 1, wherein the earth formation comprises a sensitive volume to which the magnetic field is applied and the pulsed RF energy is directed, the sensitive volume comprising at least one of water, salt water, drilling fluid, minerals, clay, mud, oil and formation fluids.

6. A method for estimating an internal gradient of an earth formation in response to a magnetic field, the method comprising:
    applying the magnetic field to the earth formation;
    directing pulsed RF energy for a first frequency to the earth formation and acquiring a first signal and directing pulsed RF energy to the earth formation for a second frequency and acquiring a second signal;
    determining a first signal decay corresponding to the first signal and a second signal decay corresponding to the second signal; and
using the first signal decay and the second signal decay to estimate the internal gradient, wherein using the determinations comprises solving a relationship for the internal gradient, $G_{int}$, the relationship comprising:

$$\frac{E_{k,1}}{E_{k,2}} = \exp\left(+\frac{\xi \cdot D(\gamma \cdot G_{int,2} \cdot TE_2)^2 t_k}{12}\right);$$

where
$E_{k,1}$ represents the first signal decay;
$E_{k,2}$ represents the second signal decay;
$TE_2$ represents a signal time for the second signal;
D represents a diffusion constant;
$\gamma$ represents a gyromagnetic ratio;
$t_k$ represents time at a formation of a $k^{th}$ echo;
$G_{int,2}$ represents the internal gradient for the second frequency; and
$\xi$ represents a configuration coefficient.

7. A method for estimating an internal gradient of an earth formation in response to a magnetic field, the method comprising:
    applying the magnetic field to the earth formation;
    directing pulsed RF energy for a first frequency to the earth formation and acquiring a first signal and directing pulsed RF energy to the earth formation for a second frequency and acquiring a second signal;
    determining a first signal decay corresponding to the first signal and a second signal decay corresponding to the second signal; and
using the first signal decay and the second signal decay to estimate the internal gradient, wherein the using the determinations comprises solving a relationship for the internal gradient, $G_{int}$, the relationship comprising:

$$\frac{1}{T_{2LM,1}} - \frac{1}{T_{2LM,2}} = \frac{\xi \cdot D(\gamma \cdot TE_2 \cdot G_{int,2})^2}{12}$$

where
$T_{2LM,1}$ represents a log-mean transverse relaxation time for the first signal;
$T_{2LM,2}$ represents the log-mean transverse relaxation time for the second signal;
TE represents a signal time for the first signal;
D represents a diffusion constant;
$\gamma$ represents a gyromagnetic ratio;

$G_{int}$, represents the internal gradient for the first frequency; and

ξ represents a configuration coefficient.

8. A computer program product stored on machine readable tangible media, the product comprising instructions for estimating an internal gradient of an earth formation in response to a magnetic field, the instructions comprising instructions for:

applying the magnetic field to the earth formation;

directing pulsed RF energy for a first frequency to the earth formation and acquiring a first signal and directing pulsed RF energy to the earth formation for a second frequency and acquiring a second signal;

determining a first signal decay corresponding to the first signal and a second signal decay corresponding to the second signal;

using the first signal decay and the second signal decay to estimate the internal gradient; and providing the estimation as an output, wherein the using the determinations comprises solving a relationship for the internal gradient, $G_{int}$, the relationship comprising:

$$\frac{E_{k,1}}{E_{k,2}} = \exp\left(-\frac{D(\gamma \cdot G_{int,1} \cdot TE_1)^2 t_k}{12}\right) \Big/ \exp\left(-\frac{D(\gamma \cdot G_{int,2} \cdot TE_2)^2 t_k}{12}\right)$$

where $E_{k,1}$ represents the first signal decay;

$E_{k,2}$ represents the second signal decay;

$TE_1$ represents a signal time for the first signal;

$TE_2$ represents a signal time for the second signal;

D represents a diffusion constant;

γ represents a gyromagnetic ratio;

$t_k$ represents time at a formation of a $k^{th}$ echo;

$G_{int,1}$ represents the internal gradient for the first frequency; and $G_{int,2}$ represents the internal gradient for the second frequency.

9. The computer program product of claim 8, wherein at least one of the first signal and the second signal comprise one of an echo-train and a portion of an echo-train.

10. The computer program product of claim 8, wherein directing pulsed RF energy for the second frequency comprises directing pulsed RF energy comprising signal times that are proportionally related to signal times of the pulsed RF energy for the first frequency.

11. The computer program product of claim 10, wherein each of the signal times comprises inter-echo times.

12. The computer program product as in claim 8, wherein the earth formation comprises a sensitive volume to which the magnetic field is applied and the pulsed RF energy is directed, the sensitive volume comprising at least one of water, salt water, drilling fluid, minerals, clay, mud, oil and formation fluids.

13. The computer program product as in claim 8, wherein providing the output comprises providing output to at least one of a screen, a printer, a memory, a network, a storage, a wireless link and a direct link.

14. A computer program product stored on machine readable tangible media, the product comprising instructions for estimating an internal gradient of an earth formation in response to a magnetic field, the instructions comprising instructions for:

applying the magnetic field to the earth formation;

directing pulsed RF energy for a first frequency to the earth formation and acquiring a first signal and directing pulsed RF energy to the earth formation for a second frequency and acquiring a second signal;

determining a first signal decay corresponding to the first signal and a second signal decay corresponding to the second signal;

using the first signal decay and the second signal decay to estimate the internal gradient; and providing the estimation as an output, wherein the using the determinations comprises solving a relationship for the internal gradient, $G_{int}$, the relationship comprising:

$$\frac{E_{k,1}}{E_{k,2}} = \exp\left(+\frac{\xi \cdot D(\gamma \cdot G_{int,2} \cdot TE_2)^2 t_k}{12}\right);$$

where $E_{k,1}$ represents the first signal decay;

$E_{k,2}$ represents the second signal decay;

$TE_2$ represents a signal time for the second signal;

D represents a diffusion constant;

γ represents a gyromagnetic ratio;

$t_k$ represents time at a formation of a $k^{th}$ echo;

$G_{int,2}$ represents the internal gradient for the another frequency; and

ξ represents a configuration coefficient.

15. A computer program product stored on machine readable tangible media, the product comprising instructions for estimating an internal gradient of an earth formation in response to a magnetic field, the instructions comprising instructions for:

applying the magnetic field to the earth formation;

directing pulsed RF energy for a first frequency to the earth formation and acquiring a first signal and directing pulsed RF energy to the earth formation for a second frequency and acquiring a second signal;

determining a first signal decay corresponding to the first signal and a second signal decay corresponding to the second signal;

using the first signal decay and the second signal decay to estimate the internal gradient; and providing the estimation as an output, wherein using the determinations comprises solving a relationship for the internal gradient, $G_{int}$, the relationship comprising:

$$\frac{1}{T_{2LM,1}} - \frac{1}{T_{2LM,2}} = \frac{\xi \cdot D(\gamma \cdot TE_2 \cdot G_{int,2})^2}{12}.$$

where $T_{2LM,1}$ represents a log-mean transverse relaxation time for the first signal;

$T_{2LM,2}$ represents the log-mean transverse relaxation time for the second signal;

TE represents a signal time for the first signal;

D represents a diffusion constant;

γ represents a gyromagnetic ratio;

$G_{int,1}$ represents the internal gradient for the first frequency; and

ξ represents a configuration coefficient.

16. A method for typing a material using diffusion based nuclear magnetic resonance (NMR) techniques, the method comprising:

applying a magnetic field to the material;

directing pulsed RF energy for a first frequency to the material and acquiring a first signal and directing pulsed RF energy to the material for a second frequency and acquiring a second signal;

determining a first signal decay corresponding to the first signal and a second signal decay corresponding to the second signal;

using the first signal decay and the second signal decay to estimate an internal gradient; and estimating a material type for the material based on the internal gradient, wherein the material comprises an earth formation, and wherein using the determinations comprises solving a relationship for the internal gradient, $G_{int}$, the relationship comprising:

$$\frac{E_{k,1}}{E_{k,2}} = \exp\left(-\frac{D(\gamma \cdot G_{int,1} \cdot TE_1)^2 t_k}{12}\right) \bigg/ \exp\left(-\frac{D(\gamma \cdot G_{int,2} \cdot TE_2)^2 t_k}{12}\right);$$

where
$E_{k,1}$ represents the first signal decay;
$E_{k,2}$ represents the second signal decay;
$TE_1$ represents a signal time for the first signal;
$TE_2$ represents a signal time for the second signal;
D represents a diffusion constant;
γ represents a gyromagnetic ratio;
$t_k$ represents time at a formation of a $k^{th}$ echo;
$G_{int,1}$ represents the internal gradient for the first frequency; and
$G_{int,2}$ represents the internal gradient for the second frequency.

17. The method as in claim 16, wherein the material comprises at least one of fresh water, salt water, drilling fluid, minerals, clay, mud, oil and a formation fluid.

18. The method as in claim 17, wherein the minerals comprise at least one of detrital minerals comprising $SiO_2$, $Ca_2CO_3$, $Mn_2O_3$ and secondary minerals comprising at least one of a type of clay mineral and a type of evaporate mineral.

19. The method as in claim 16, wherein at least one of the first signal and the second signal comprise one of an echo-train and a portion of an echo-train.

20. The method as in claim 16, wherein directing pulsed RF energy for the second frequency comprises directing pulsed RF energy comprising signal times that are proportionally related to signal times of the pulsed RF energy for the first frequency.

21. The method as in claim 20, wherein each of the signal times comprises inter-echo times.

22. A method for typing a material using diffusion based nuclear magnetic resonance (NMR) techniques, the method comprising:

applying a magnetic field to the material;

directing pulsed RF energy for a first frequency to the material and acquiring a first signal and directing pulsed RF energy to the material for a second frequency and acquiring a second signal;

determining a first signal decay corresponding to the first signal and a second signal decay corresponding to the second signal;

using the first signal decay and the second signal decay to estimate an internal gradient; and estimating a material type for the material based on the internal gradient, wherein the material comprises an earth formation, and wherein using the determinations comprises solving a relationship for the internal gradient, $G_{int}$, the relationship comprising:

$$\frac{E_{k,1}}{E_{k,2}} = \exp\left(+\frac{\xi \cdot D(\gamma \cdot G_{int,2} \cdot TE_2)^2 t_k}{12}\right);$$

where
$E_{k,1}$ represents the first signal decay;
$E_{k,2}$ represents the second signal decay;
$TE_2$ represents a signal time for the second signal;
D represents a diffusion constant;
γ represents a gyromagnetic ratio;
$t_k$ represents time at a formation of a $k^{th}$ echo;
$G_{int,2}$ represents the internal gradient for the second frequency; and
ξ represents a configuration coefficient.

23. A method for typing a material using diffusion based nuclear magnetic resonance (NMR) techniques, the method comprising:

applying a magnetic field to the material;

directing pulsed RF energy for a first frequency to the material and acquiring a first signal and directing pulsed RF energy to the material for a second frequency and acquiring a second signal;

determining a first signal decay corresponding to the first signal and a second signal decay corresponding to the second signal;

using the first signal decay and the second signal decay to estimate an internal gradient; and estimating a material type for the material based on the internal gradient, wherein the material comprises an earth formation, and wherein the using the determinations comprises solving a relationship for the internal gradient, $G_{int}$, the relationship comprising:

$$\frac{1}{T_{2LM,1}} - \frac{1}{T_{2LM,2}} = \frac{\xi \cdot D(\gamma \cdot TE_2 \cdot G_{int,2})^2}{12}$$

where
$T_{2LM,1}$ represents a log-mean transverse relaxation time for the first signal;
$T_{2LM,2}$ represents the log-mean transverse relaxation time for the second signal;
TE represents a signal time for the first signal;
D represents a diffusion constant;
γ represents a gyromagnetic ratio;
$G_{int,2}$ represents the internal gradient for the second frequency; and
ξ represents a configuration coefficient.

* * * * *